US008353901B2

(12) United States Patent
Rossetto et al.

(10) Patent No.: US 8,353,901 B2
(45) Date of Patent: Jan. 15, 2013

(54) ENERGY DELIVERY CONDUITS FOR USE WITH ELECTROSURGICAL DEVICES

(75) Inventors: Francesca Rossetto, Longmont, CO (US); Mani N. Prakash, Boulder, CO (US); Brian Shiu, Sunnyvale, CA (US)

(73) Assignee: Vivant Medical, Inc., Boulder, CO (US)

( * ) Notice: Subject to any disclaimer, the term of this patent is extended or adjusted under 35 U.S.C. 154(b) by 1638 days.

(21) Appl. No.: 11/805,052

(22) Filed: May 22, 2007

(65) Prior Publication Data
US 2008/0294162 A1 Nov. 27, 2008

(51) Int. Cl.
*A61B 18/04* (2006.01)
*A61B 18/18* (2006.01)

(52) U.S. Cl. ............................. 606/33; 606/40; 174/68.1

(58) Field of Classification Search .................. 333/241, 333/243; 174/68.1, 70 R, 126.1, 128.1; 606/32, 606/33, 34, 40, 45, 49, 50
See application file for complete search history.

(56) References Cited

U.S. PATENT DOCUMENTS

| | | |
|---|---|---|
| 4,140,130 A | 2/1979 | Storm, III |
| 4,311,154 A | 1/1982 | Sterzer et al. |
| 4,409,993 A | 10/1983 | Furihata |
| 4,534,347 A | 8/1985 | Taylor |
| 4,557,272 A | 12/1985 | Carr |
| 4,583,869 A | 4/1986 | Chive et al. |
| 4,612,940 A | 9/1986 | Kasevich et al. |
| 4,621,642 A | 11/1986 | Chen |
| 4,658,836 A | 4/1987 | Turner |
| 4,700,716 A | 10/1987 | Kasevich et al. |
| 4,776,086 A | 10/1988 | Kasevich et al. |
| 4,800,899 A | 1/1989 | Elliott |
| 4,823,812 A | 4/1989 | Eshel et al. |
| 4,841,988 A | 6/1989 | Fetter et al. |
| 4,945,912 A | 8/1990 | Langberg |
| 5,097,845 A | 3/1992 | Fetter et al. |
| 5,122,137 A | 6/1992 | Lennox |
| 5,190,054 A | 3/1993 | Fetter et al. |
| 5,221,269 A | 6/1993 | Miller et al. |
| 5,234,004 A | 8/1993 | Hascoet et al. |
| 5,246,438 A | 9/1993 | Langberg |

(Continued)

FOREIGN PATENT DOCUMENTS

EP 0 521 264 1/1993

(Continued)

OTHER PUBLICATIONS

I Chou, C.K., "Radiofrequency Hyperthermia in Cancer Therapy," Biologic Effects of Nonionizing Electromagnetic Fields, Chapter 94, CRC Press, Inc., (1995), pp. 1424-1428.

(Continued)

*Primary Examiner* — Dean O Takaoka
*Assistant Examiner* — Alan Wong

(57) ABSTRACT

A conduit assembly for transmitting energy between an electrosurgical energy generator and an energy delivering device comprises a first cable sub-assembly including a cable having a flexibility and an energy attenuation; a second cable sub-assembly including a cable having a flexibility and an energy attenuation; wherein the flexibility of the cable of the first cable sub-assembly is less than the flexibility of the cable of the second cable sub-assembly; and wherein the energy attenuation of the cable of the first cable sub-assembly is less than the energy attenuation of the cable of the second cable sub-assembly.

30 Claims, 4 Drawing Sheets

U.S. PATENT DOCUMENTS

| | | |
|---|---|---|
| 5,249,585 A | 10/1993 | Mody et al. |
| 5,275,597 A | 1/1994 | Higgins et al. |
| 5,281,217 A | 1/1994 | Edwards et al. |
| 5,301,687 A | 4/1994 | Wong et al. |
| 5,314,466 A | 5/1994 | Stern et al. |
| 5,342,355 A | 8/1994 | Long |
| 5,344,441 A | 9/1994 | Gronauer |
| 5,366,490 A | 11/1994 | Edwards et al. |
| 5,370,644 A | 12/1994 | Langberg |
| 5,383,922 A | 1/1995 | Zipes et al. |
| 5,405,346 A | 4/1995 | Grundy et al. |
| 5,413,588 A | 5/1995 | Rudie et al. |
| 5,458,597 A | 10/1995 | Edwards et al. |
| 5,464,445 A | 11/1995 | Rudie et al. |
| 5,480,417 A | 1/1996 | Hascoet et al. |
| 5,500,012 A | 3/1996 | Daniel et al. |
| 5,507,743 A | 4/1996 | Coen et al. |
| 5,509,929 A | 4/1996 | Hascoet et al. |
| 5,520,684 A | 5/1996 | Imran |
| 5,536,267 A | 7/1996 | Edwards et al. |
| 5,545,137 A | 8/1996 | Rudie et al. |
| 5,556,377 A | 9/1996 | Rosen et al. |
| 5,599,294 A | 2/1997 | Edwards et al. |
| 5,599,295 A | 2/1997 | Rosen et al. |
| 5,628,770 A | 5/1997 | Thome et al. |
| 5,683,382 A | 11/1997 | Lenihan et al. |
| 5,720,718 A | 2/1998 | Rosen et al. |
| 5,741,249 A | 4/1998 | Moss et al. |
| 5,755,754 A | 5/1998 | Rudie et al. |
| 5,776,176 A | 7/1998 | Rudie |
| 5,800,486 A | 9/1998 | Thome et al. |
| 5,810,803 A | 9/1998 | Moss et al. |
| 5,810,804 A | 9/1998 | Rudie et al. |
| 5,829,519 A | 11/1998 | Uthe |
| 5,843,144 A | 12/1998 | Rudie et al. |
| 5,871,523 A | 2/1999 | Fleischman et al. |
| 5,897,554 A | 4/1999 | Hall et al. |
| 5,902,251 A | 5/1999 | vanHooydonk |
| 5,904,691 A | 5/1999 | Barnett et al. |
| 5,904,709 A | 5/1999 | Arndt et al. |
| 5,916,240 A | 6/1999 | Rudie et al. |
| 5,931,807 A | 8/1999 | McClure et al. |
| 5,938,692 A | 8/1999 | Rudie |
| 5,951,547 A | 9/1999 | Gough et al. |
| 5,957,969 A | 9/1999 | Warner et al. |
| 5,964,755 A | 10/1999 | Edwards |
| 5,974,343 A | 10/1999 | Brevard et al. |
| 5,980,563 A | 11/1999 | Miller et al. |
| 5,997,532 A | 12/1999 | McLaughlin et al. |
| 6,016,811 A | 1/2000 | Turner et al. |
| 6,026,331 A | 2/2000 | Brucker et al. |
| 6,032,078 A | 2/2000 | Rudie |
| 6,047,216 A | 4/2000 | Carl et al. |
| 6,056,744 A | 5/2000 | Sharkey et al. |
| 6,059,780 A | 5/2000 | Edwards et al. |
| 6,063,078 A | 5/2000 | Wittkampf |
| 6,073,051 A | 6/2000 | Thome et al. |
| 6,080,150 A | 6/2000 | Gough et al. |
| 6,097,985 A | 8/2000 | Kasevich et al. |
| 6,106,518 A | 8/2000 | Chia et al. |
| 6,122,551 A | 9/2000 | Tu et al. |
| 6,134,476 A | 10/2000 | Arndt et al. |
| 6,146,379 A | 11/2000 | Knopp et al. |
| 6,176,856 B1 | 1/2001 | Jandak et al. |
| 6,181,970 B1 | 1/2001 | Kasevich |
| 6,217,528 B1 | 4/2001 | Feldberg et al. |
| 6,223,086 B1 | 4/2001 | Gough et al. |
| 6,226,553 B1 | 5/2001 | Carl et al. |
| 6,233,490 B1 | 5/2001 | Kasevich |
| 6,235,048 B1 | 5/2001 | Dobak, III |
| 6,245,064 B1 | 6/2001 | Sharkey et al. |
| 6,251,128 B1 | 6/2001 | Gough |
| 6,275,738 B1 | 8/2001 | Kasevich et al. |
| 6,277,113 B1 | 8/2001 | Berube |
| 6,289,249 B1 | 9/2001 | Arndt et al. |
| 6,290,715 B1 | 9/2001 | Wittenberger et al. |
| 6,306,132 B1 | 10/2001 | Rudie et al. |
| 6,325,796 B1 | 12/2001 | Fleischman et al. |
| 6,330,479 B1 | 12/2001 | Stauffer |
| 6,346,104 B2 | 2/2002 | Daly et al. |
| 6,347,251 B1 | 2/2002 | Deng |
| 6,350,262 B1 | 2/2002 | Ashley |
| 6,355,033 B1 | 3/2002 | Koblish et al. |
| 6,383,182 B1 | 5/2002 | Berube et al. |
| 6,405,733 B1 | 6/2002 | Fogarty et al. |
| 6,461,352 B2 * | 10/2002 | Morgan et al. ................. 606/34 |
| 6,471,696 B1 | 10/2002 | Berube et al. |
| 6,496,737 B2 | 12/2002 | Rudie et al. |
| 6,496,738 B2 | 12/2002 | Carr |
| 6,512,956 B2 | 1/2003 | Arndt et al. |
| 6,514,251 B1 | 2/2003 | Carl et al. |
| 6,530,922 B2 | 3/2003 | Cosman et al. |
| 6,547,788 B1 * | 4/2003 | Maguire et al. ................. 606/41 |
| 6,564,806 B1 | 5/2003 | Fogarty et al. |
| 6,569,159 B1 | 5/2003 | Edwards et al. |
| 6,589,234 B2 | 7/2003 | Lalonde et al. |
| 6,592,579 B2 | 7/2003 | Arndt et al. |
| 6,663,624 B2 | 12/2003 | Lesh et al. |
| 6,675,050 B2 | 1/2004 | Arndt et al. |
| 6,685,700 B2 | 2/2004 | Behl et al. |
| 6,699,241 B2 | 3/2004 | Rappaport et al. |
| 6,706,040 B2 | 3/2004 | Mahon et al. |
| 6,722,371 B1 | 4/2004 | Fogarty et al. |
| 6,752,154 B2 | 6/2004 | Fogarty et al. |
| 6,752,767 B2 | 6/2004 | Turovskiy et al. |
| 6,823,218 B2 | 11/2004 | Berube |
| 6,852,091 B2 | 2/2005 | Edwards et al. |
| 6,878,147 B2 | 4/2005 | Prakash et al. |
| 7,128,739 B2 | 10/2006 | Prakash et al. |
| 7,147,632 B2 | 12/2006 | Prakash et al. |
| 7,174,217 B2 | 2/2007 | Rioux et al. |
| 7,190,989 B1 | 3/2007 | Swanson et al. |
| 7,207,985 B2 | 4/2007 | Duong et al. |
| 7,217,282 B2 | 5/2007 | Ginsburg et al. |
| 7,229,437 B2 | 6/2007 | Johnson et al. |
| 7,231,259 B2 | 6/2007 | Jenney et al. |
| 7,234,225 B2 | 6/2007 | Johnson et al. |
| 7,234,977 B2 | 6/2007 | Westlund et al. |
| 7,235,070 B2 | 6/2007 | Vanney |
| 7,238,166 B2 | 7/2007 | Callister |
| 7,238,184 B2 | 7/2007 | Megerman et al. |
| 7,238,194 B2 | 7/2007 | Monstadt et al. |
| 7,241,293 B2 | 7/2007 | Davison |
| 7,244,254 B2 | 7/2007 | Brace et al. |
| 7,245,955 B2 | 7/2007 | Rashidi |
| 7,264,619 B2 | 9/2007 | Venturelli |
| 7,270,656 B2 | 9/2007 | Gowda et al. |
| 7,270,658 B2 | 9/2007 | Woloszko et al. |
| 7,270,659 B2 | 9/2007 | Ricart et al. |
| 7,270,661 B2 | 9/2007 | Dahla et al. |
| 7,270,662 B2 | 9/2007 | Visram et al. |
| 7,271,363 B2 | 9/2007 | Lee et al. |
| 7,273,480 B2 | 9/2007 | Young et al. |
| 7,276,061 B2 | 10/2007 | Schaer et al. |
| 7,282,049 B2 | 10/2007 | Orszulak et al. |
| 7,285,116 B2 | 10/2007 | de la Rama |
| 7,293,562 B2 | 11/2007 | Malecki et al. |
| 7,300,438 B2 | 11/2007 | Falwell et al. |
| 7,301,131 B2 | 11/2007 | Gauthier et al. |
| 7,306,592 B2 | 12/2007 | Morgan et al. |
| 7,309,325 B2 | 12/2007 | Mulier et al. |
| 7,309,336 B2 | 12/2007 | Ashley et al. |
| 7,311,702 B2 | 12/2007 | Tallarida et al. |
| 7,311,703 B2 | 12/2007 | Turovskiy et al. |
| 7,311,705 B2 | 12/2007 | Sra |
| 7,317,949 B2 | 1/2008 | Morrison et al. |
| 7,318,822 B2 | 1/2008 | Darmos et al. |
| 7,318,823 B2 | 1/2008 | Sharps et al. |
| 7,318,824 B2 | 1/2008 | Parakash et al. |
| 7,319,904 B2 | 1/2008 | Cross, Jr. et al. |
| 7,326,204 B2 | 2/2008 | Paul et al. |
| 7,326,205 B2 | 2/2008 | Paul et al. |
| 7,326,206 B2 | 2/2008 | Paul et al. |
| 7,331,957 B2 | 2/2008 | Woloszko et al. |
| 7,337,009 B2 | 2/2008 | Schell |
| 7,465,300 B2 * | 12/2008 | Arless et al. ................. 606/21 |
| 7,601,149 B2 * | 10/2009 | DiCarlo et al. ................. 606/34 |

| | | |
|---|---|---|
| 2001/0001819 A1 | 5/2001 | Lee et al. |
| 2001/0008966 A1 | 7/2001 | Arndt et al. |
| 2001/0020178 A1 | 9/2001 | Arndt et al. |
| 2001/0020180 A1 | 9/2001 | Arndt et al. |
| 2001/0037812 A1 | 11/2001 | Dobak, III et al. |
| 2002/0022832 A1 | 2/2002 | Mikus et al. |
| 2002/0087151 A1 | 7/2002 | Mody et al. |
| 2002/0133148 A1 | 9/2002 | Daniel et al. |
| 2002/0147444 A1 | 10/2002 | Shah et al. |
| 2002/0198520 A1 | 12/2002 | Coen et al. |
| 2003/0004506 A1 | 1/2003 | Messing |
| 2003/0065317 A1 | 4/2003 | Lee et al. |
| 2003/0069578 A1 | 4/2003 | Dobak, III et al. |
| 2003/0078573 A1 | 4/2003 | Truckai et al. |
| 2003/0088242 A1 | 5/2003 | Prakash et al. |
| 2003/0109862 A1 | 6/2003 | Prakash et al. |
| 2003/0195499 A1 | 10/2003 | Prakash et al. |
| 2004/0078038 A1 | 4/2004 | Desinger et al. |
| 2004/0167517 A1 | 8/2004 | Desinger et al. |
| 2004/0168692 A1 | 9/2004 | Fogarty et al. |
| 2004/0243200 A1 | 12/2004 | Turner et al. |
| 2004/0267156 A1 | 12/2004 | Turovskiy et al. |
| 2005/0015081 A1 | 1/2005 | Turovskiy et al. |
| 2005/0065508 A1 | 3/2005 | Johnson et al. |
| 2005/0085881 A1 | 4/2005 | Prakash et al. |
| 2005/0107783 A1 | 5/2005 | Tom et al. |
| 2005/0148836 A1 | 7/2005 | Kleen et al. |
| 2005/0159741 A1 | 7/2005 | Paul et al. |
| 2006/0259024 A1 | 11/2006 | Turovskiy et al. |
| 2006/0264923 A1 | 11/2006 | Prakash et al. |
| 2006/0282069 A1 | 12/2006 | Prakash et al. |
| 2007/0027451 A1 | 2/2007 | Desinger et al. |
| 2007/0073282 A1 | 3/2007 | McGaffigan et al. |
| 2007/0123765 A1 | 5/2007 | Hetket et al. |
| 2007/0129715 A1 | 6/2007 | Eggers et al. |
| 2007/0135879 A1 | 6/2007 | McIntyre et al. |
| 2007/0142829 A1 | 6/2007 | Ahn et al. |
| 2007/0149964 A1 | 6/2007 | Kawabata et al. |
| 2007/0156048 A1 | 7/2007 | Panescu et al. |
| 2007/0156128 A1 | 7/2007 | Jimenez |
| 2007/0156132 A1 | 7/2007 | Drysen |
| 2007/0156133 A1 | 7/2007 | McDaniel et al. |
| 2007/0173680 A1 | 7/2007 | Rioux et al. |
| 2007/0173798 A1 | 7/2007 | Adams et al. |
| 2007/0173812 A1 | 7/2007 | Bonan et al. |
| 2007/0179375 A1 | 8/2007 | Fuimaono et al. |
| 2007/0179497 A1 | 8/2007 | Eggers et al. |
| 2007/0185478 A1 | 8/2007 | Cosentino |
| 2007/0191825 A1 | 8/2007 | Cronin et al. |
| 2007/0203551 A1 | 8/2007 | Cronin et al. |
| 2007/0208334 A1 | 9/2007 | Woloszko et al. |
| 2007/0208335 A1 | 9/2007 | Woloszko et al. |
| 2007/0208383 A1 | 9/2007 | Williams |
| 2007/0213700 A1 | 9/2007 | Davison et al. |
| 2007/0213703 A1 | 9/2007 | Naam et al. |
| 2007/0215163 A1 | 9/2007 | Harrington et al. |
| 2007/0219551 A1 | 9/2007 | Honour et al. |
| 2007/0225701 A1 | 9/2007 | O'Sullivan |
| 2007/0233057 A1 | 10/2007 | Konishi |
| 2007/0244529 A1 | 10/2007 | Choi et al. |
| 2007/0250053 A1 | 10/2007 | Fernald et al. |
| 2007/0250054 A1 | 10/2007 | Drake |
| 2007/0250055 A1 | 10/2007 | Johnson et al. |
| 2007/0250056 A1 | 10/2007 | Vanney |
| 2007/0255276 A1 | 11/2007 | Sliwa, Jr. et al. |
| 2007/0260235 A1 | 11/2007 | Podhajsky |
| 2007/0260237 A1 | 11/2007 | Sutton et al. |
| 2007/0270679 A1 | 11/2007 | Nguyen et al. |
| 2007/0270791 A1 | 11/2007 | Wang et al. |
| 2007/0276361 A1 | 11/2007 | Stevens-Wright et al. |
| 2007/0276362 A1 | 11/2007 | Rioux et al. |
| 2007/0282323 A1 | 12/2007 | Woloszko et al. |
| 2007/0282324 A1 | 12/2007 | Vaska et al. |
| 2007/0282325 A1 | 12/2007 | Young et al. |
| 2007/0287995 A1 | 12/2007 | Mayse |
| 2007/0287998 A1 | 12/2007 | Sharareh et al. |
| 2007/0293853 A1 | 12/2007 | Truckai et al. |
| 2007/0293854 A1 | 12/2007 | Pless et al. |
| 2007/0293855 A1 | 12/2007 | Sliwa, Jr. et al. |
| 2007/0299488 A1 | 12/2007 | Carr |
| 2008/0004614 A1 | 1/2008 | Burdette et al. |
| 2008/0004618 A1 | 1/2008 | Johnson et al. |

FOREIGN PATENT DOCUMENTS

| | | |
|---|---|---|
| EP | 0 667 126 | 8/1995 |
| WO | WO 93/20767 | 10/1993 |
| WO | WO 93/20768 A1 | 10/1993 |
| WO | WO 96/34571 | 11/1996 |
| WO | WO 97/48449 | 12/1997 |
| WO | WO 97/48450 | 12/1997 |
| WO | WO 97/48451 | 12/1997 |
| WO | WO 99/56642 | 11/1999 |
| WO | WO 99/56643 | 11/1999 |
| WO | WO 99/56812 | 11/1999 |
| WO | WO 00/49957 | 8/2000 |
| WO | WO 00/57811 | 10/2000 |
| WO | WO 01/60235 | 8/2001 |
| WO | WO 02/078777 | 10/2002 |
| WO | WO 03/034932 | 5/2003 |
| WO | WO 03/039385 | 5/2003 |
| WO | WO 03/047043 A1 | 6/2003 |
| WO | WO 03/088806 | 10/2003 |
| WO | WO 03/088858 | 10/2003 |
| WO | WO 2005/011049 | 2/2005 |

OTHER PUBLICATIONS

International Search Report—EP 06 00 9435 dated Jul. 13, 2006.
US 5,326,343, 07/1994, Rudie et al. (withdrawn)

* cited by examiner

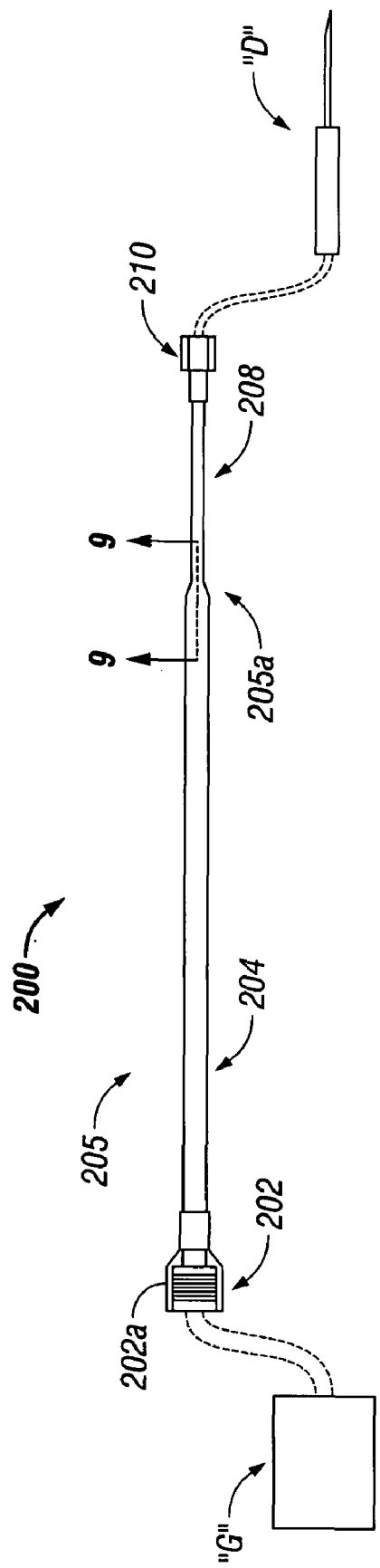
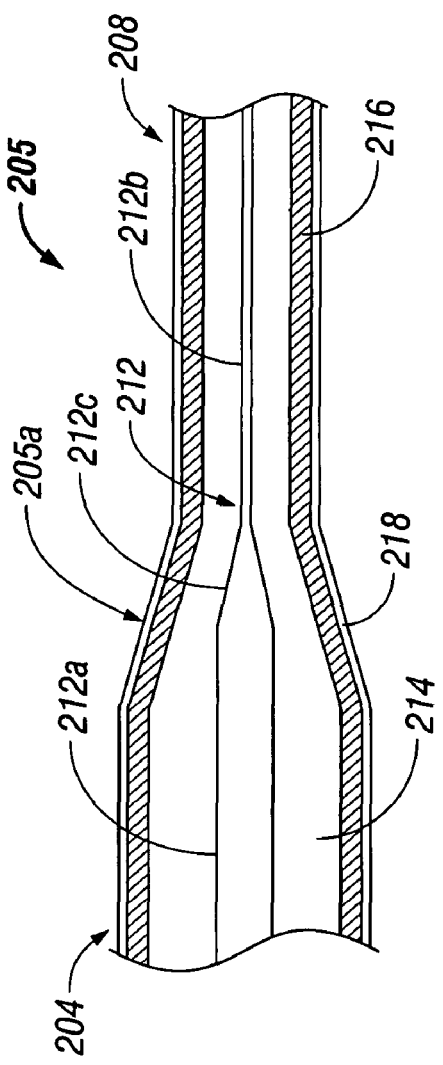
FIG. 8
FIG. 9

ENERGY DELIVERY CONDUITS FOR USE WITH ELECTROSURGICAL DEVICES

BACKGROUND

1. Technical Field

The present disclosure relates to electrosurgical systems, and more particularly, to energy delivery conduits for use with electrosurgical devices during RF and/or microwave ablation procedures.

2. Background Of Related Art

Energy delivery conduits, including coaxial cables are well known in the art and its applications are numerous. Coaxial cables are typically used, in surgical procedures, to transfer energy from one point to another while minimizing losses during said transmission.

Although many kinds of coaxial cables have been designed, for the most part, these devices serve primarily as energy transmission conduits. Aside from transmitting energy, it is often desirable to have coaxial cables with different characteristics and features.

SUMMARY

The present disclosure relates to a conduit assembly for transmitting electrosurgical energy between an electrosurgical generator and an energy delivering device. The conduit assembly comprises a first cable sub-assembly including a cable; and a second cable sub-assembly including a cable. The flexibility of the cable of the first cable sub-assembly is less than the flexibility of the cable of the second cable sub-assembly. Further, the energy attenuation of the cable of the first cable sub-assembly is less than the energy attenuation of the cable of the second cable sub-assembly. In one embodiment, the diameter of the first cable sub-assembly is larger than the diameter of the second cable sub-assembly. In another embodiment, the length of the first cable sub-assembly is greater than the length of the second cable sub-assembly.

The conduit assembly may further include a connector assembly. The connector assembly includes a first connector operatively connected to a first end of the cable of the first cable sub-assembly and a second connector operatively connected to the second end of the cable of the second cable sub-assembly. The first and second connecters are matable with one another to electrically connect the cable of the first cable sub-assembly with the cable of the second cable sub-assembly.

Additionally, the cable of the first cable sub-assembly includes an inner conductor surrounded by a dielectric material and an outer conductor surrounding the dielectric material. The cable of the second cable sub-assembly also includes an inner conductor surrounded by a dielectric material and an outer conductor surrounding the dielectric material.

BRIEF DESCRIPTION OF THE DRAWINGS

Embodiments of the presently disclosed conduit assemblies are disclosed herein with reference to the drawings, wherein:

FIG. 8 is a side elevational view of a conduit assembly according to a further embodiment of the present disclosure shown attached between an energy delivering device and an electrosurgical energy generator; and FIG. 9 is a longitudinal cross-sectional view of a portion of the conduit assembly of FIG. 8, as taken through 9-9 of FIG. 8.

DETAILED DESCRIPTION OF EMBODIMENTS

Figure 1:
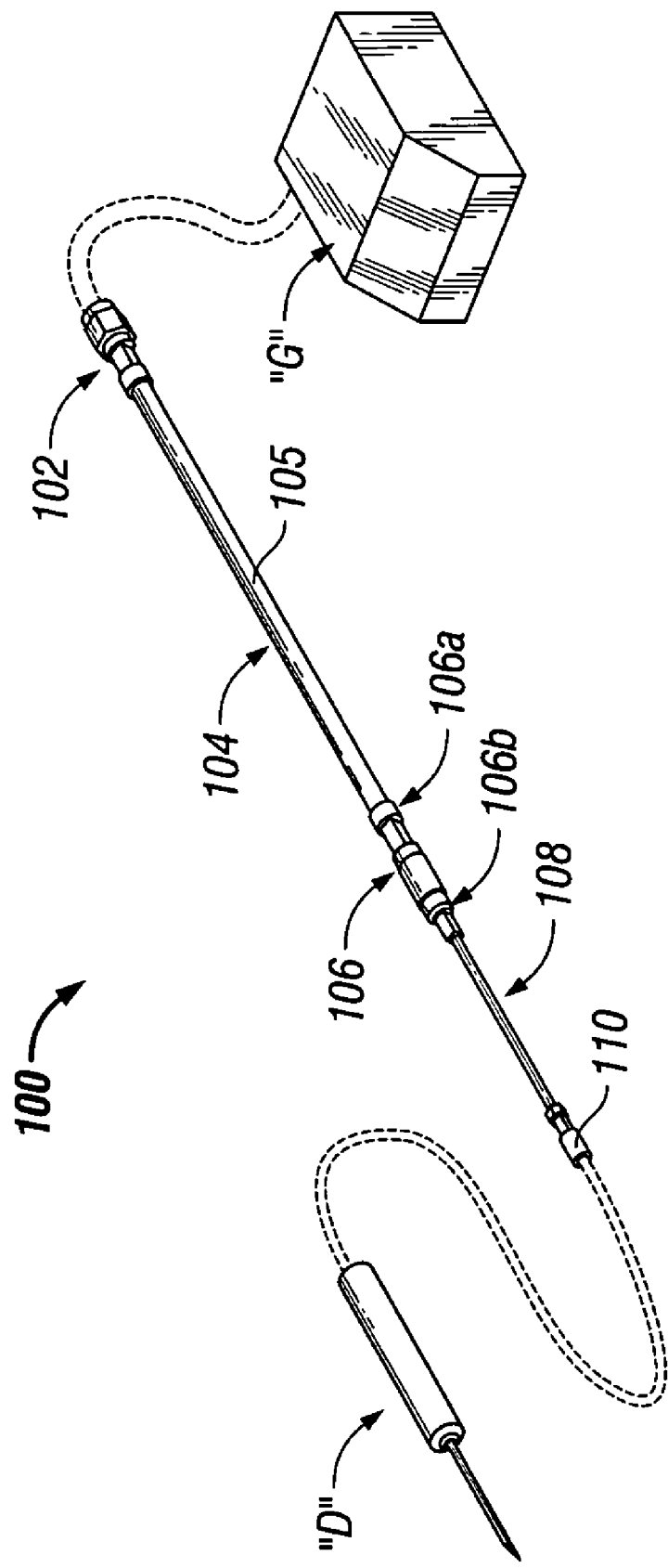
FIG. 1 is a perspective view of a conduit assembly according to an embodiment of the present disclosure shown attached between an energy delivering device and an electrosurgical energy generator.

Embodiments of the presently disclosed energy transmission conduit assembly are now described in detail with reference to the drawings, in which like reference numerals designate identical or corresponding elements in each of the several views. As used herein, the terms "distal" refers to that portion of the conduit assembly, or component thereof, farther from the user while the term "proximal" refers to that portion of the component thereof, closest to the user.

Electrosurgical energy delivering systems employ electrosurgical energy (e.g., RF or microwave) to ablate tissue at a specific target site. During electrosurgical procedures, electrosurgical energy delivering systems directly apply therapeutic energy to a desired tissue location to ablate said tissue.

Electrosurgical energy delivering systems include an electrosurgical energy generator "G" (i.e., RF and/or microwave generator), an energy delivery device or instrument "D" having a probe, needle, antenna, and/or knife and at least one energy delivery conduit interconnecting the energy delivering device "D" and the generator "G".

The energy transmission conduit assembly hereinbelow described is intended to be used with a microwave energy delivering system. It is contemplated, however, that the energy transmission conduit assembly described below may be utilized with any suitable electrosurgical system known in the art. The described energy transmission conduit assembly is designed to minimize loss of energy along or throughout a length thereof.

Referring initially to FIGS. 1-5, an energy transmission conduit assembly in accordance with an embodiment of the present disclosure, is generally referred to as reference numeral 100. Conduit assembly 100 includes a first cable sub-assembly 104 configured and adapted for connection to an electrosurgical energy generator "G" via a generator connector 102, a second cable sub-assembly 108 configured and adapted for connection to an energy delivering device "D" via a device connector 110, and a cable connector assembly 106 configured and adapted to interconnect first cable sub-assembly 104 and second cable sub-assembly 108 to one another.

Figure 2:
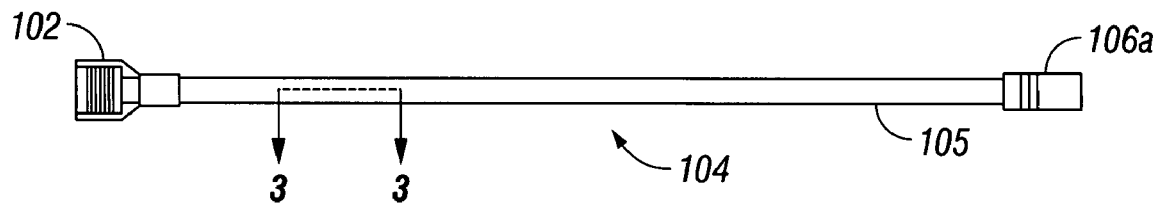
FIG. 2 is a side elevational view of a first cable assembly of the conduit assembly of FIG. 1.

As seen in FIG. 2, first cable sub-assembly 104 includes a cable 105 configured to transmit electrosurgical energy, a generator connector 102 operatively connected to a first end of cable 105 and configured and adapted for connection to generator "G", and a first connector 106a of cable connector 106 operatively connected to a second end of cable 105.

Generator connector 102 may include an insulative or dielectric covering 102a such as a polyolefin heat-shrink tubing, as depicted in FIG. 2. Other suitable dielectric materials, known by those having skill in the art, may be used to electrically insulate generator connector 102. In addition to generator connector 102, adapters (not shown) may be used to interconnect electrosurgical energy generator "G" to first cable sub-assembly 104 if generator connector 102 is not properly sized or does not properly mate with electrosurgical energy generator "G".

Figure 3:
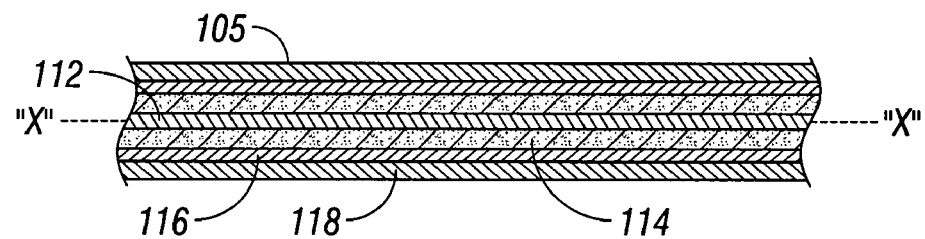
FIG. 3 is a longitudinal cross-sectional view of a portion of the first cable assembly of the conduit cable assembly of FIGS. 1 and 2, as taken through 3-3 of FIG. 2.

With reference to FIG. 3, cable 105 of first cable sub-assembly 104 comprises an inner conductor 112 surrounded by a dielectric material 114, and an outer conductor 116 surrounding dielectric material 114 and encompassed by an outer sheath 118. Dielectric material 114 may be formed of any suitable low energy loss material such as low density or ultra-density PolyTetraFluoroEthylene ("PTFE"), cellular high density polyethylene or the like. Outer sheath 118 may be comprised of any suitable electrically insulative material known in the art such as fluorinated ethylene propylene ("FEP") or polyolefin.

It is contemplated that cable 105 of first cable sub-assembly 104 may be flexible or semi-rigid. Accordingly, inner conductor 112 of cable 105 may be flexible (i.e., having a stranded transverse cross-sectional profile or any other suitable flexible structure known in the art) or semi-rigid (i.e., having a solid transverse cross-section profile or any other semi-rigid structure known in the art). Outer conductor 116 may be flexible (i.e., made of braided silver plated cooper or any other suitable material known in the art) or semi-rigid (i.e., be fabricated of solid cooper or any other suitable material known in the art).

Inner conductor 112 of first cable sub-assembly 104 may be fabricated from cooper or from any other suitable electrically conductive material. Additionally, inner conductor 112 may contain a conductive plating or the like. The conductive plating may be comprised of silver or other suitable material known in the art.

Cable 105 of first cable sub-assembly 104 may be long enough to allow a surgeon to extend it from electrosurgical energy generator "G" to the patient in a typical medical suite, while at the same time, short enough to limit energy attenuation therealong. Specifically, it is envisioned that the length of cable 105 may range from about 5 feet to about 10 feet. It is further contemplated that cable 105 may have a diameter greater than about 0.14 inches. In one embodiment, the diameter of cable 105 may measure approximately 0.20 inches.

In an alternative embodiment, cable 105 of first cable assembly 104 may be enclosed in an articulating arm that extends into and over the sterile field. The articulating arm may be part of the electrosurgical energy generator "G" or, a separate cart system. Alternatively, cable 105 may be detachably connected to the electrosurgical energy generator "G" via a fastening device such as a removable clip (not shown). The fastening device may prevent cable 105 from exerting excessive force on the energy delivering device "D". Cable 105 and/or first cable sub-assembly 104 may be reusable or disposable.

Figure 4:
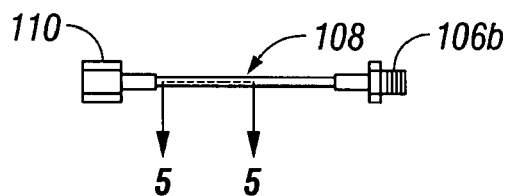
FIG. 4 is a side elevational view of second cable assembly of the conduit assembly of FIGS. 1-3.

Referring now to FIGS. 1 and 4, second cable sub-assembly 108 includes a cable 109 configured to transmit electrosurgical energy, a device connector 110 connected to a first end of cable 109 for connection to energy delivering device "D" and a second connector 106b of cable connector 106 operatively connected to a second end of cable 109 configured and adapted for selective coupling with first connector 106a of first cable sub-assembly 104. Device connector 110 may include adapters (not shown) to properly mate with energy delivering device "D" or second cable assembly 108.

Figure 5:
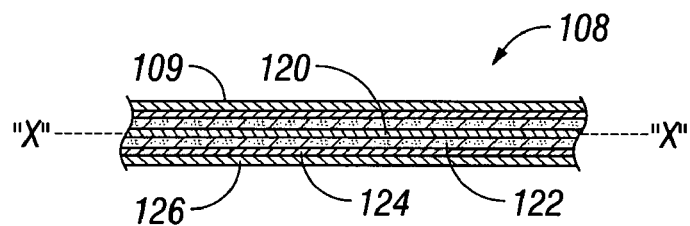
FIG. 5 is a longitudinal cross-sectional view of the second cable assembly of the conduit assembly of FIGS. 1-3, as taken through 5-5 of FIG. 4.
Figure 6:
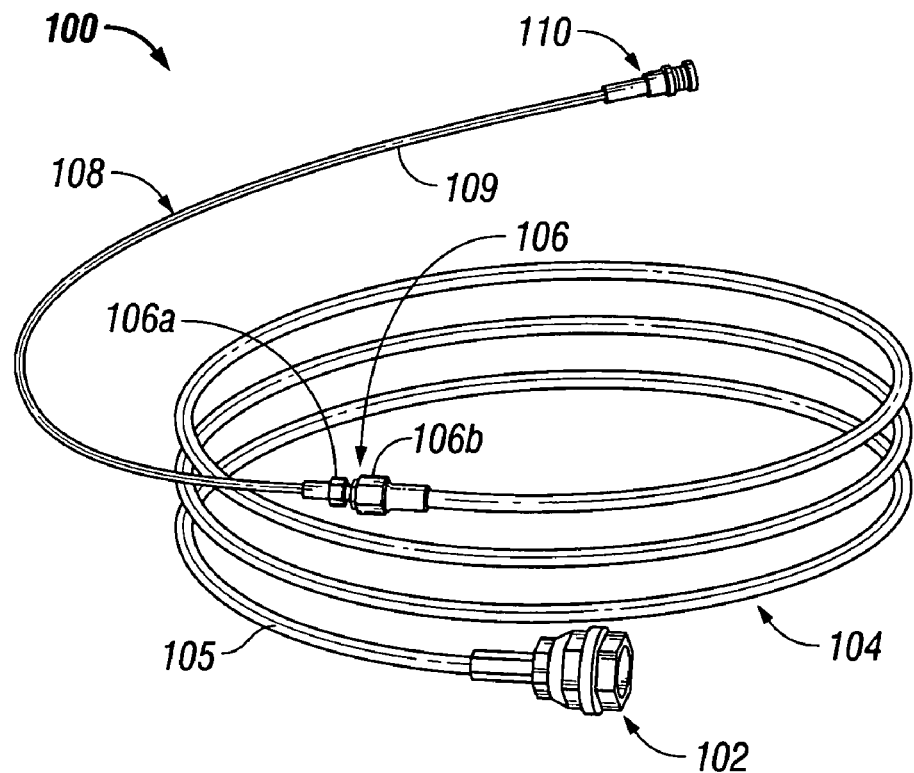
FIG. 6 is a perspective view of a conduit assembly according to another embodiment of the present disclosure.
Figure 7:
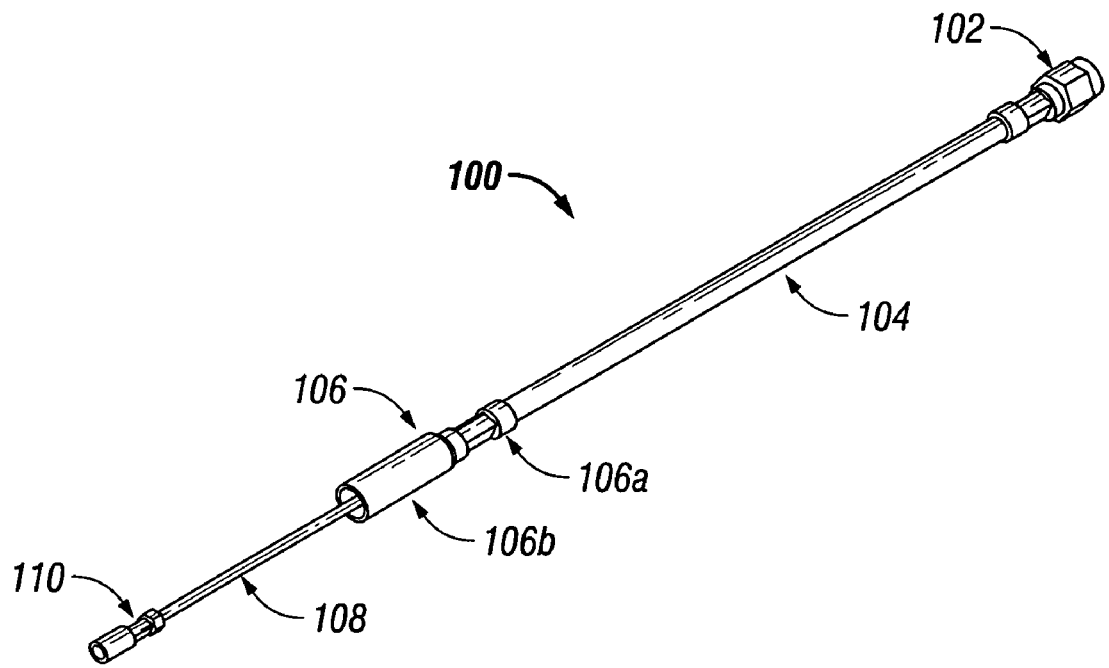
FIG. 7 is a perspective view of a conduit assembly according to still another embodiment of the present disclosure.

With reference to FIG. 5, cable 109 of second cable sub-assembly 108 comprises an inner conductor 120 surrounded by a dielectric material 122, and an outer conductor 124 surrounding dielectric material 122 and encompassed by an outer sheath 126. Outer conductor 124 and inner conductor 120 are configured as a coaxial cable. Inner conductor 120 of second cable sub-assembly 108 has a smaller diameter than inner conductor 112 of first cable sub-assembly 104. Likewise, outer conductor 124 of second cable sub-assembly 108 has a smaller diameter than outer conductor 116 of first cable sub-assembly 104. Second cable sub-assembly 108 may be reusable or disposable.

It is envisioned that cable 109 of second cable sub-assembly 108 may be flexible. Accordingly, inner conductor thereof 120 may be flexible and may have a stranded transverse cross-sectional profile. Copper or other suitable electrically conductive material may be utilized to make inner conductor 120. In an embodiment, inner conductor 120 may include a silver plating.

The length of cable 109 of second cable assembly 108 may be short enough to limit energy attenuation, but sufficiently long to allow good maneuverability of energy delivering device "D". It is envisioned that the length of cable 109 of second cable sub-assembly 108 may range from about 0.5 feet to about 2.0 feet. In one embodiment, the length of cable 109 of second cable sub-assembly 108 may measure about 12 inches. It is further contemplated that cable 109 of second cable sub-assembly 108 may have a diameter less than about 0.12 inches. In one embodiment, the diameter of cable 109 of second cable sub-assembly 108 may measure about 0.10 inches.

Dielectric material 122 of second cable sub-assembly 108 may be made of any suitable low loss dielectric material such as low density or ultra-low density PTFE, or cellular high density polyethylene. Outer conductor 124 of second cable sub-assembly 108 may be formed of braided silver plated cooper or any other suitable electrically conductive material known in the art.

In use, connectors 102, 106, 110 electrically connect electrosurgical energy generator "G", first and second cable sub-assemblies 104, 108 of conduit assembly 100, and energy delivering device "D" to one another. To facilitate electrical conductivity throughout and along conduit assembly 100, connectors 102, 106, 110 may have an impedance appropriate for the specific electrosurgical system employed. It is envisioned that each connectors 102, 106, 110 may have an impedance of about 50 Ohms. In addition, an electrically insulative material, such as polyolefin, PVC or plastic heat-shrink tubing, may be placed over connectors 102, 106, 110 to provide electrical insulation thereof, as illustrated in FIG. 2. A person skilled in the art will understand that many other kinds of suitable dielectric materials may be used to cover connectors 102, 106, 110.

Returning now to FIG. 2, the distal or first end of first cable sub-assembly 104 is connected to the proximal or second end of second cable sub-assembly 108 via first and second connectors 106a, 106b of cable connector 106. Adaptors may supplement cable connector 106 in the event that cable connector 106 does not properly mate with either first cable sub-assembly 104 or second cable sub-assembly 108. Alternatively, first cable sub-assembly 104 may be connected directly to second cable sub-assembly 108 through crimping, soldering, welding or any other suitable method as known by one skilled in the art. It will be apparent to one skilled in the art that second cable sub-assembly 108 may be connected to the energy delivering device "D" by any suitable method such as crimping, soldering, or welding.

In an alternative embodiment, the electrical connection between inner conductor 112 of first cable sub-assembly 104 and inner conductor 120 of second cable sub-assembly 108 may be achieved by crimping the inner conductor 120 over first inner conductor 112. If cable 105 of first cable sub-assembly 104 has a stranded inner conductor 112, electrical connection may be achieved by crimping the stranded inner conductor 112 over the inner conductor 120 of second cable sub-assembly 108. Electrical connection between outer conductors 116 of first cable sub-assembly 104 and outer conductor 124 of second cable sub-assembly 108 may be achieved by crimping first outer conductor 116 over second outer conductor 124, irrespective of their form.

In one embodiment, electrical connection between inner conductors 112, 120 may be achieved by soldering and/or welding the two inner conductors 112, 120 together. Outer conductors 116, 124 may also be soldered and/or welded together to achieve electrical connectivity therebetween. It is contemplated that a combination of crimping, soldering and welding may be used to connect inner conductors 112, 120 to one another and outer conductors 116, 124 to one another.

Conduit assembly 100 may have cable sub-assemblies having cables of various lengths with various energy attenuation levels. Alternatively, conduit assembly 100, having the same energy loss levels, may have cables of different sizes, diameters and/or lengths. It is envisioned that the conduit assembly 100 may have a maximum energy loss of about −3 dB at about 915 MHz.

In one embodiment, conduit cable assembly 100 may include first cable sub-assembly 104 having a cable 105 with a length of about 9 feet. Cable 105 is connected through cable connector 106 to a cable 109 of second cable sub-assembly 108 having a length of about 1 foot. Conduit cable assembly 100 also includes a generator connector 102 disposed at a proximal end thereof. As previously discussed, generator connector 102 is configured and adapted for connection to electrosurgical energy generator "G". Generator connector 102 may include an insulative or dielectric covering 102a such as a polyolefin heat-shrink tubing. A device connector 110 is disposed at the distal end of the conduit assembly 100 and is configured and adapted for connection to electrosurgical energy delivery device "D". Cable 105 may have an energy attenuation of about −0.14 dB/foot at about 915 MHz. In turn, cable 109 may have an energy attenuation of about −0.25 dB/foot at about 915 MHz. Each connector 102, 106, 110 may have an energy attenuation of about −0.07 dB at about 915 MHz. In this embodiment, the total energy attenuation at about 915 MHz may be about −1.79 dB. This embodiment may be used particularly for percutaneous applications.

In a further embodiment, conduit assembly 100 has a first cable sub-assembly 104 having a cable 105 with a length of about 6 feet. Cable 105 is connected through cable connector 106 to a cable 109 of second cable sub-assembly 108 having a length of about 1 foot. Conduit assembly 100 may have a generator connector 102 disposed at the proximal end thereof and a device connecter 110 disposed at the distal end thereof. Generator connector 102 is configured and adapted for connection to an electrosurgical energy generator "G". Device connector 110 is configured and adapted for connection to an energy delivering device "D." In this embodiment, cable 105 has an energy attenuation of about −0.14 dB/foot at about 915 MHz. Cable 109 has an energy attenuation of about −0.25 dB/foot at about 915 MHz. Each connector 102, 106, 110 may have an energy attenuation of about −0.07 dB at about 915 MHz. The total energy attenuation in this embodiment may be about −1.37 dB. This embodiment may be used particularly for surgical applications. While the figures of the present disclosure illustrate a conduit assembly 100 with only two cables, it is contemplated that more than two cables may be used to attain the desired combination of energy attenuation and assembly flexibility.

In use, first cable sub-assembly 104 allows transmission of electrosurgical energy from electrosurgical energy generator "G" to second cable sub-assembly 108. Cable connector 106 interconnects first cable sub-assembly 104 and second cable sub-assembly 108. To achieve low energy losses, the impedance of cable 105 of first cable sub-assembly 104 must be appropriate for the specific electrosurgical system used. For example, in one embodiment, first cable 105 of first cable sub-assembly 104 has an impedance of about 50 Ohms.

Moreover, cable 105 of second cable sub-assembly 108 has a higher degree of flexibility than cable 109 of first cable sub-assembly 104. However, cable 105 of first cable sub-assembly 108 has lower energy attenuation than cable 109 of second cable sub-assembly 104. Such a design provides conduit assembly 100 with good maneuverability, while at the same time, limits energy losses between electrosurgical energy generator "G" and energy delivering device "D".

In operation, energy delivering device "D" is connected to electrosurgical energy generator "G" through conduit assembly 100 and receives electrosurgical energy from energy generator "G". During operation, conduit assembly 100 minimizes the energy attenuation along its length, thereby maximizing the energy transmitted to energy delivering device "D", and limiting heating of conduit assembly 100. Moreover, the flexibility of conduit assembly 100 allows a surgeon to easily maneuver energy delivering device "D" during clinical procedures.

Turning now to FIGS. 8 and 9, a conduit assembly according to another embodiment of the disclosure is generally designated as 200. Conduit assembly 200 is substantially similar to conduit assembly 100 and thus will only be discussed in detail herein to the extent necessary to identify differences in construction and operation.

As seen in FIGS. 8 and 9, conduit assembly 200 comprises a single cable 205 having a variable diameter along its length. Cable 205 includes a first or proximal section 204, a transition section 205a and a second or distal section 208. First section 204 has a diameter greater than a diameter of second section 208. Accordingly, a flexibility of second section 208 may be relatively higher than a flexibility of first section 204. In addition, first section 204 may have a relatively lower energy attenuation than second section 208.

Transition section 205a varies in diameter between first section 204 and second section 208. A proximal end of transition section 205a has a diameter equal to the diameter of first section 204. A distal end of transition section 205a has a diameter equal to the diameter of second section 208.

First section 204 is connectable to an electrosurgical energy generator "G" via a generator connector 202. Generator connector 202 may include an insulative or dielectric covering 202a such as a polyolefin heat-shrink tubing. Second section 208, in turn, is connectable to an energy delivering device "D" via device connector 210.

As seen in FIG. 9, cable 205 comprises an inner conductor 212 surrounded by a dielectric material 214, an outer conductor 216 surrounding dielectric material 214, and an outer sheath 218 encompassing outer conductor 216. Inner conductor 212 includes a first section 212a having a first diameter, a second section 212b having a second diameter, and transition section 212c interconnecting the first and second sections 212a, 212b.

It is envisioned that cable 205 may be flexible or semi-rigid. Accordingly, inner conductor 212 of cable 205 may be flexible (i.e., having a stranded transverse cross-sectional profile or any other suitable flexible structure known in the art) or semi-rigid (i.e., having a solid transverse cross-sectional profile or any other semi-rigid structure known in the art). Cooper or other suitable electrically conductive material may be utilized to make inner conductor 212. Inner conductor 212 may also include silver plating. Outer conductor 216 may be flexible (i.e., made of braided silver plated cooper or any other suitable material known in the art) or semi-rigid (i.e., be fabricated of solid cooper or any other suitable material known in the art).

Dielectric material 214 may be formed of any suitable low energy loss material such as low density or ultra-density PolyTetraFluoroEthylene ("PTFE"), cellular high density polyethylene or the like. Outer sheath 218 may be comprised of any suitable electrically insulative material known in the art such as fluorinated ethylene propylene ("FEP") or polyolefin. Conduit assembly 200 may have, for example, a total energy loss of about −1.79 dB or −1.37 dB.

Energy delivering device "D" may be used for surgical procedures entailing microwave ablation. However, the applications of the conduit assemblies and methods of using the conduit assemblies, discussed above, are not limited thereto, but may include any number of further electrosurgical applications. Modifications of the above-described conduit assembly and the same, and variations of aspects of the disclosure that are obvious to those of skill in the art are intended to be within the scope of the claims.

What is claimed is:

1. A conduit assembly for transmitting electrosurgical energy between an electrosurgical generator and an energy delivering device, the conduit assembly comprising:
   a first cable sub-assembly including a cable having a flexibility and an energy attenuation; and
   a second cable sub-assembly including a cable having a flexibility and an energy attenuation;
   wherein the flexibility of the cable of the first cable sub-assembly is less than the flexibility of the cable of the second cable sub-assembly; and
   wherein the energy attenuation of the cable of the first cable sub-assembly is less than the energy attenuation of the cable of the second cable sub-assembly.

2. The conduit assembly according to claim 1, wherein the cable of the first cable sub-assembly has a diameter and the cable of the second cable sub-assembly has a diameter less than the diameter of the cable of the first cable sub-assembly.

3. The conduit assembly according to claim 1, wherein the cable of the first cable sub-assembly has a length, and the cable of the second cable sub-assembly has length less than the length of the cable of the first cable sub-assembly.

4. The conduit assembly according to claim 2, wherein the cable of the first cable sub-assembly has a length, and the cable of the second cable sub-assembly has length less than the length of the cable of the first cable sub-assembly.

5. The conduit assembly according to claim 1, further comprising a connector assembly having a first connector operatively connected to a first end of the cable of the first cable sub-assembly and a second connector operatively connected to a second end of the cable of the second cable sub-assembly, wherein the first and second connectors are matable with one another to electrically connect the cable of the first cable sub-assembly with the cable of the second cable sub-assembly.

6. The conduit assembly according to claim 1, wherein the cable of the first cable sub-assembly includes an inner conductor surrounded by a dielectric material, and an outer conductor surrounding the dielectric material; and
   wherein the cable of the second cable sub-assembly includes an inner conductor surrounded by a dielectric material, and an outer conductor surrounding the dielectric material.

7. The conduit assembly according to claim 1, wherein the conduit assembly has an energy loss of about −1.79 dB.

8. The conduit assembly according to claim 1, wherein the first cable sub-assembly has an energy loss of about −0.14 dB per foot at about 915 MHz and a length of about 9 feet; and
   wherein the second cable sub-assembly has an energy loss of about −0.25 dB per foot at about 915 MHz and a length of about 1 foot.

9. The conduit assembly according to claim 1, wherein the conduit assembly has an energy loss of about −1.37 dB.

10. The conduit assembly according to claim 1, wherein the first cable sub-assembly has an energy loss of about −0.14 dB per foot at about 915 MHz and a length of about 6 feet; and
    wherein the second cable sub-assembly has an energy loss of about −0.25 dB per foot at about 915 MHz and a length of about 1 foot.

11. The conduit assembly according to claim 5, wherein the connector assembly has a total energy loss of about −0.07 dB.

12. A conduit assembly for transmitting energy, comprising:
    a first cable sub-assembly including a proximal and distal ends, the proximal end being configured and adapted for connection to an electrosurgical energy generator, the first cable sub assembly including:
      a first cable having:
        a first inner conductor disposed within the cable;
        a first outer conductor disposed within the cable, wherein the first inner conductor and the first outer conductor are configured as a coaxial cable; and
        a first dielectric material disposed between first inner conductor and first outer conductor;
        wherein the first cable has a first flexibility and a first energy attenuation;
    a second cable sub-assembly including proximal and distal ends, the proximal end being configured and adapted for interconnecting the first cable sub-assembly and second cable sub-assembly, and the distal end configured to be operatively connected to an energy delivering device, the second cable sub-assembly including:
      a second cable having:
        a second inner conductor disposed within the cable;
        a second outer conductor disposed within the cable, wherein the second inner and the second outer conductors are configured as a coaxial cable; and
        wherein the second cable has a second flexibility and a second energy attenuation;
    wherein the second flexibility is greater than the first flexibility, and wherein the second energy attenuation is greater than the first energy attenuation.

13. The conduit assembly according to claim 12, wherein the first cable has a first diameter and the second cable has a second diameter.

14. The conduit assembly according to claim 12, wherein the first diameter is greater than the second diameter.

15. The conduit assembly according to claim 12, wherein the first inner conductor includes a conductive plating surrounding the first inner conductor.

16. The conduit assembly according to claim 12, wherein the second inner conductor includes a conductive plating surrounding the first inner conductor.

17. The conduit assembly according to claim 12, further comprising a first connector interconnecting the distal end of the first cable sub-assembly and the proximal end of the second cable sub-assembly.

18. A method of delivering energy in a surgical site between an electrosurgical energy generator and an energy delivering device, the method comprising the steps of:
   providing a conduit assembly operatively interconnecting the electrosurgical energy generator and the energy delivering device, the conduit assembly including:
   a first cable sub-assembly including a cable having a flexibility and an energy attenuation;
   a second cable sub-assembly including a cable a flexibility and an energy attenuation;
   wherein the flexibility of the cable of the first cable sub-assembly is less than the flexibility of the cable of the second cable sub-assembly; and
   wherein the energy attenuation of the cable of the first cable sub-assembly is less than the energy attenuation of the cable of the second cable sub-assembly;
   supplying to the energy delivering device from the electrosurgical energy generator via the conduit assembly;
   wherein the conduit assembly has a total energy loss of about −1.79 dB.

19. The method of delivering energy according to claim 18, wherein first cable sub-assembly has a total energy loss of about −1.26 dB; and
   wherein the second cable sub-assembly has a total energy loss of about −0.25 dB.

20. The method of delivering energy according to claim 18, wherein the step of providing a conduit assembly further includes a connector assembly connecting the first and second sub-assemblies and having a total energy loss of about −0.07 dB.

21. A method of delivering energy in a surgical site between an electrosurgical energy generator and an energy delivering device, the method comprising the steps of:
   providing a conduit assembly operatively interconnecting the electrosurgical energy generator and the energy delivering device, the conduit assembly including:
   a first cable sub-assembly including a cable having a flexibility and an energy attenuation;
   a second cable sub-assembly including a cable a flexibility and an energy attenuation;
   wherein the flexibility of the cable of the first cable sub-assembly is less than the flexibility of the cable of the second cable sub-assembly; and
   wherein the energy attenuation of the cable of the first cable sub-assembly is less than the energy attenuation of the cable of the second cable sub-assembly;
   supplying to the energy delivering device from the electrosurgical energy generator via the conduit assembly;
   wherein the conduit assembly has a total energy loss of about −1.37 dB.

22. The method of delivering energy according to claim 21, wherein the first cable sub-assembly has a total energy loss of about −0.84 dB.

23. The method of delivering energy according to claim 21, wherein the step of providing a conduit assembly further includes a connector assembly connecting the first and second sub-assemblies and having a total energy loss of about −0.07 dB.

24. A conduit assembly for transmitting electrosurgical energy between an electrosurgical generator and an energy delivering device, the conduit assembly comprising:
   a cable including:
      a first section having a flexibility, a diameter and an energy attenuation; and
      a second section having a flexibility, a diameter and an energy attenuation;
      a transition section interposed between the first section and the second section, the transition section varying in diameter between the first section and the second section;
   wherein the diameter of the first section is greater than the diameter of the second section;
   wherein the flexibility of the first section is less than the flexibility of the second section; and
   wherein the energy attenuation of the first section is less than the energy attenuation of the second section.

25. The conduit assembly according to claim 24, wherein the cable includes an inner conductor, dielectric material surrounding the inner conductor, and an outer conductor surrounding the dielectric material.

26. The conduit assembly according to claim 24, wherein the cable includes a generator connector for connecting the proximal end of the cable and an electrosurgical energy generator.

27. The conduit assembly according to claim 24, wherein the cable includes a device connector for connecting the distal end of the cable to an energy delivery device.

28. The conduit assembly according to claim 24, wherein the conduit assembly has an energy loss of about −1.79 dB.

29. The conduit assembly according to claim 24, wherein the conduit assembly has an energy loss of about −1.37 dB.

30. The conduit assembly according to claim 25, wherein the inner conductor includes a first section having a first diameter, a second section having a second diameter, and a transition section interconnecting the first and second sections.

* * * * *